United States Patent
Jahnke et al.

(10) Patent No.: US 9,151,698 B2
(45) Date of Patent: Oct. 6, 2015

(54) TESTING SYSTEM FOR EXAMINING TURBINE BLADES

(75) Inventors: Ronny Jahnke, Falkensee (DE); Tristan Sczepurek, Berlin (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 21 days.

(21) Appl. No.: 13/638,993

(22) PCT Filed: Dec. 16, 2010

(86) PCT No.: PCT/EP2010/069947
§ 371 (c)(1),
(2), (4) Date: Oct. 2, 2012

(87) PCT Pub. No.: WO2011/131263
PCT Pub. Date: Oct. 27, 2011

(65) Prior Publication Data
US 2013/0026365 A1   Jan. 31, 2013

(30) Foreign Application Priority Data
Apr. 23, 2010   (DE) .......... 10 2010 018 013

(51) Int. Cl.
*G01M 99/00* (2011.01)
*G01N 25/72* (2006.01)
(Continued)

(52) U.S. Cl.
CPC .......... *G01M 99/002* (2013.01); *F01D 25/285* (2013.01); *G01B 11/24* (2013.01); *G01N 25/72* (2013.01); *B23P 2700/06* (2013.01)

(58) Field of Classification Search
CPC .......... G01J 2005/0077; G01J 5/0088; G01M 3/002; G01N 2021/8887; G01N 21/95692; G01N 2201/102; G01N 25/72; G06T 2207/10048; G06T 2207/30164; G06T 7/0006; G06T 7/0042
USPC ....................................... 250/338.1
See application file for complete search history.

(56) References Cited

U.S. PATENT DOCUMENTS 5,111,046 A   5/1992   Bantel
5,125,035 A *  6/1992   McCarthy et al. ............ 382/141
(Continued)

FOREIGN PATENT DOCUMENTS

EP   1475629 A1   11/2004
EP   1739409 A1    1/2007
(Continued)

OTHER PUBLICATIONS

Derwent World Patents Index, Ultrasonic defect inspection method for three dimensional casting goods such as forge blade, machining blade, etc of gas turbine engines involves performing ultrasonic inspection, Dec. 2000, Derwent Acct. No. 2000131562, pp. 5-6 English Analysis.*
(Continued)

*Primary Examiner* — David Porta
*Assistant Examiner* — Jeremy S Valentiner

(57) ABSTRACT

A testing system for examining the coating and open cooling-air holes of turbine blades includes a positioning device for an infrared camera with two degrees of freedom, a rotating-pivoting device for positioning the turbine blade, and a rotatable air duct arranged on the rotating-pivoting device. The rotatable air duct is configured for introducing into the turbine blade air at a temperature higher or lower in comparison with the turbine blade.

14 Claims, 8 Drawing Sheets

(51) Int. Cl.
*F01D 25/28* (2006.01)
*G01B 11/24* (2006.01)

(56) References Cited

U.S. PATENT DOCUMENTS

| | | | |
|---|---|---|---|
| 6,610,992 B1 * | 8/2003 | Macaulay et al. | 250/559.22 |
| 2004/0119018 A1 * | 6/2004 | Alfano et al. | 250/341.1 |
| 2006/0291716 A1 * | 12/2006 | Vaidyanathan | 382/152 |
| 2007/0276629 A1 * | 11/2007 | Koonankeil | 702/185 |
| 2008/0237466 A1 | 10/2008 | Key | |
| 2009/0285359 A1 * | 11/2009 | Saigusa et al. | 378/61 |
| 2010/0017015 A1 * | 1/2010 | Morii | 700/213 |

FOREIGN PATENT DOCUMENTS

| | | |
|---|---|---|
| EP | 1767743 A1 | 3/2007 |
| EP | 1898209 A1 | 3/2008 |
| JP | 2000002693 A * | 1/2000 |
| WO | WO 9805949 A1 | 2/1998 |
| WO | WO 03038403 A2 | 5/2003 |
| WO | WO 2007034814 A1 * | 3/2007 |
| WO | WO 2008069203 A1 * | 6/2008 |

OTHER PUBLICATIONS

Becker, English Translation of WO 98/05949 from IDS dated Oct. 2, 2012 from Espacenet.com, retrieved Feb. 20, 2014, pp. 1-4, available at http://translationportal.epo.org/emtp/translate/?ACTION=description-retrieval&COUNTRY=WO&ENGINE=google&FORMAT=docdb&KIND=A1&LOCALE=en_EP&NUMBER=9805949&OPS=ops.epo.org&SRCLANG=de&TRGLANG=en.*

Collins German-English Dictionary Definition for Ankoppeln, retrieved from http://dictionary.reverso.net/german-english/ankoppln on Feb. 20, 2014, 5th Edition 2004, p. 1.*

* cited by examiner

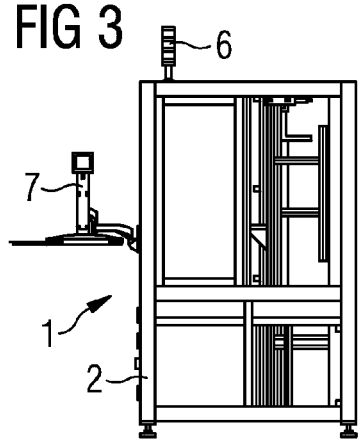
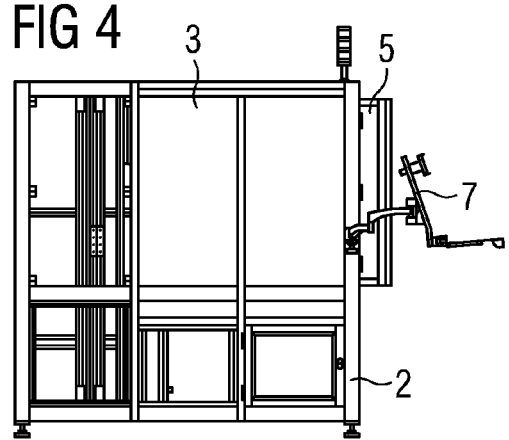
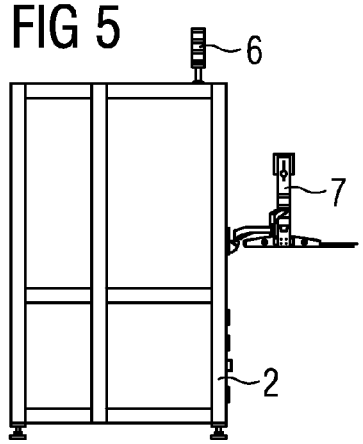
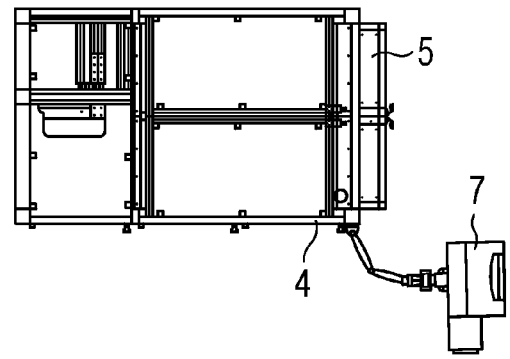
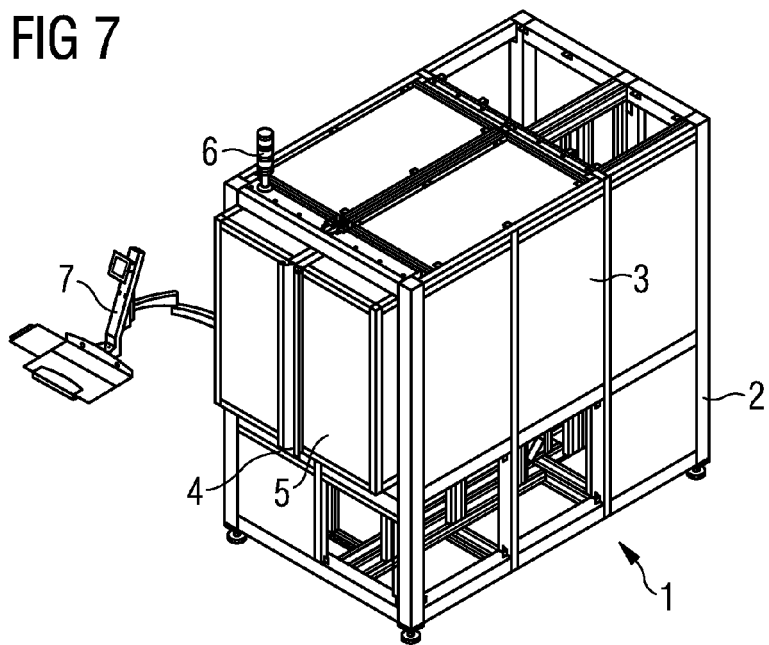

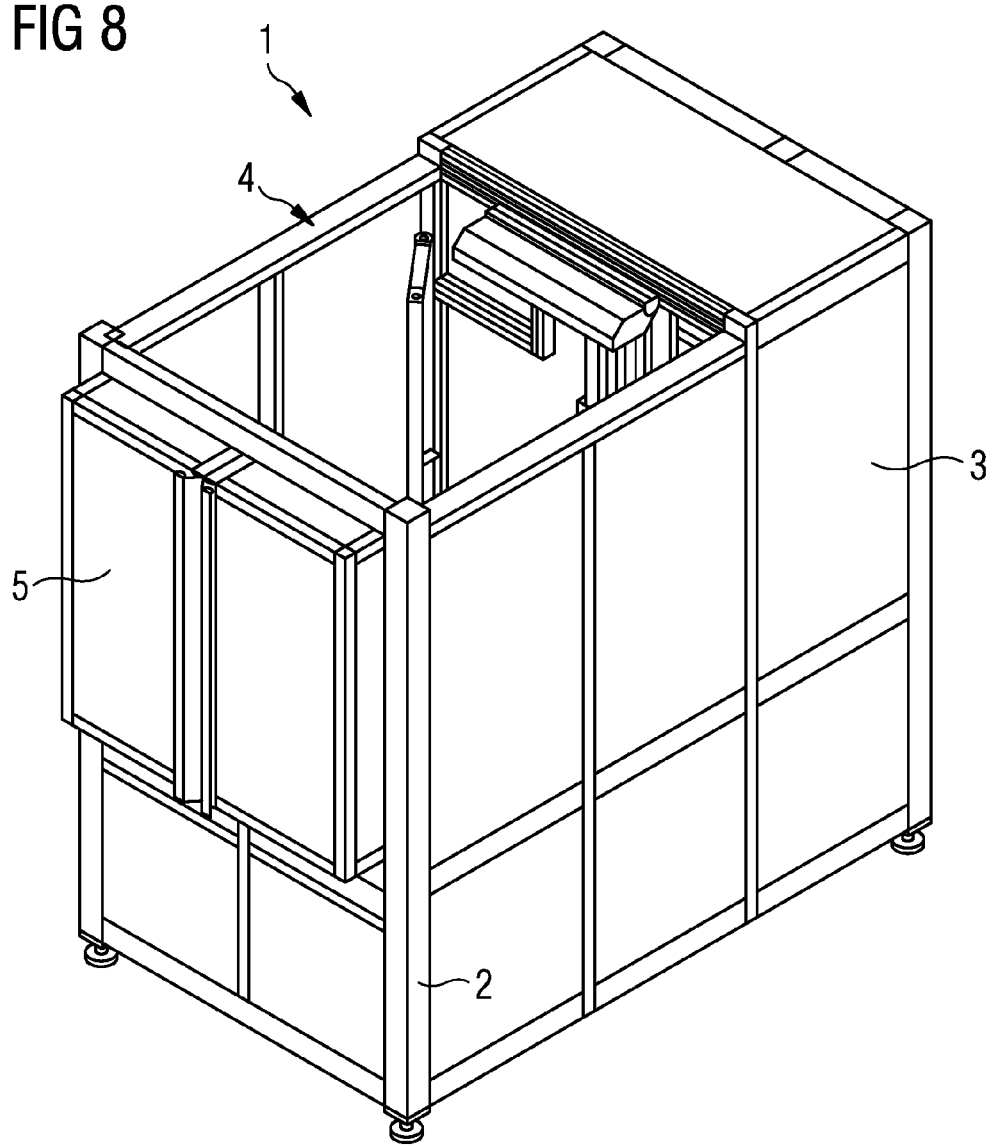

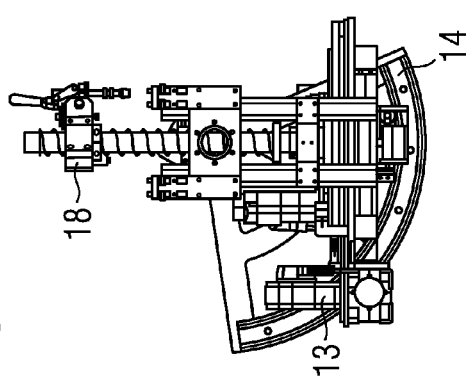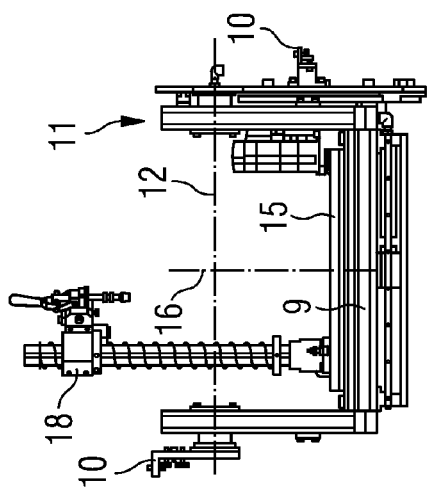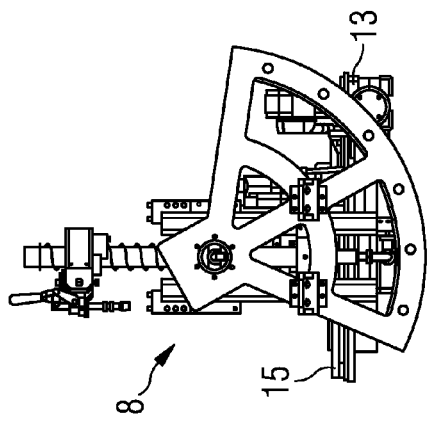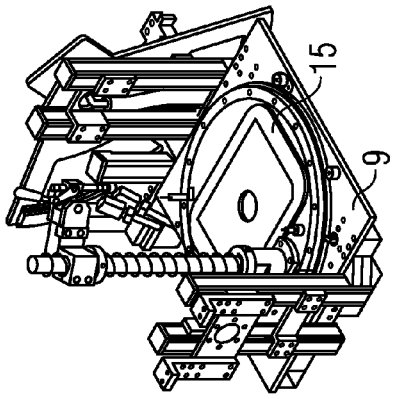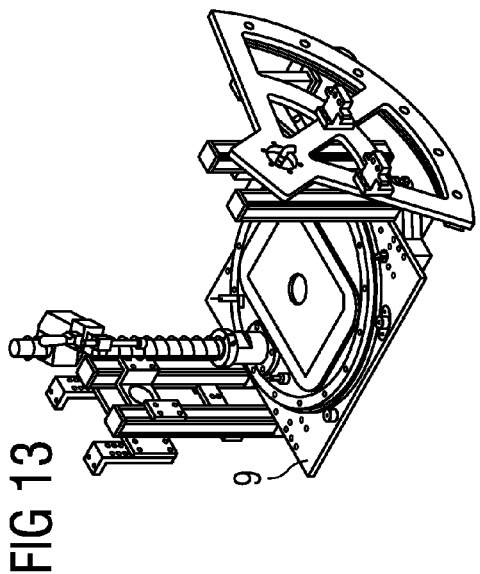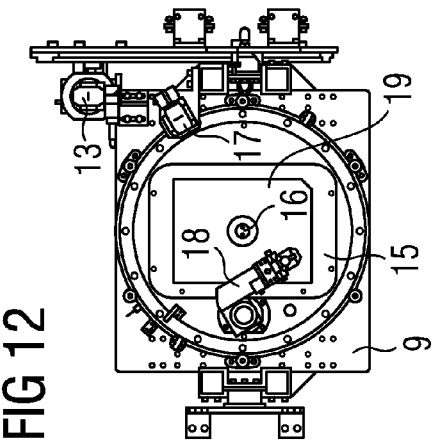

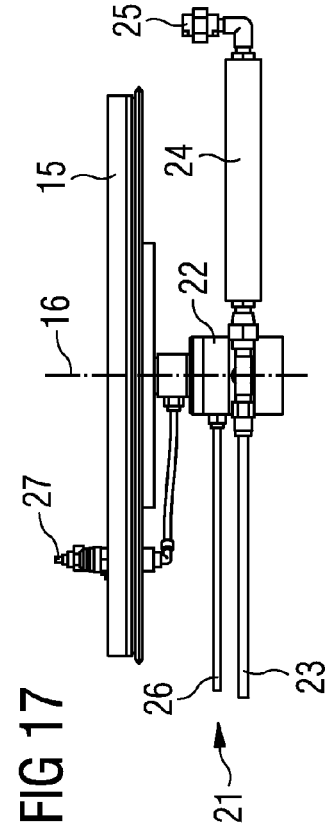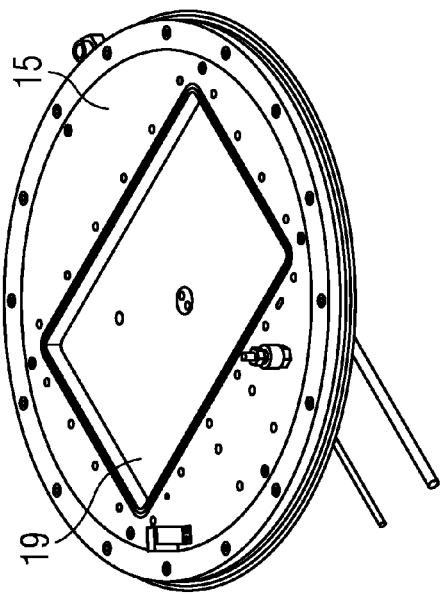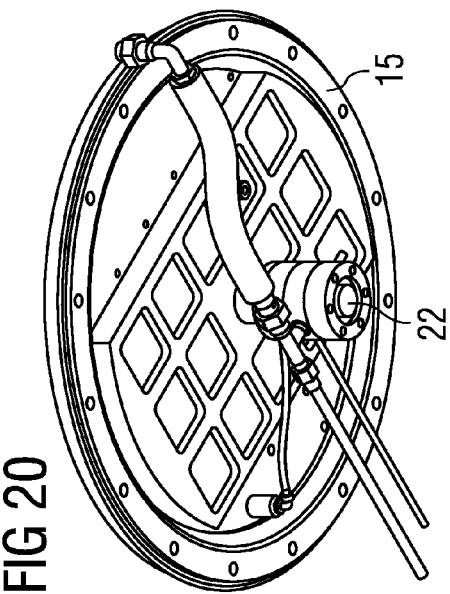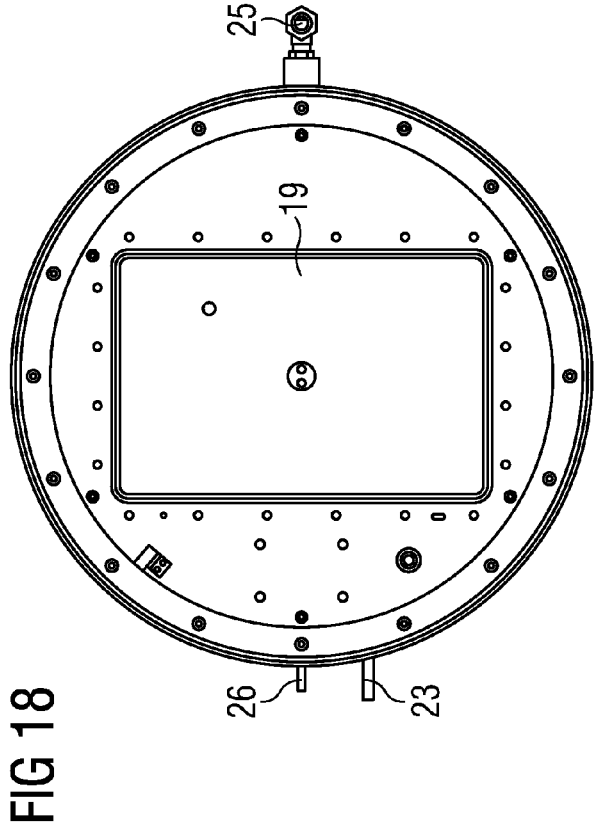

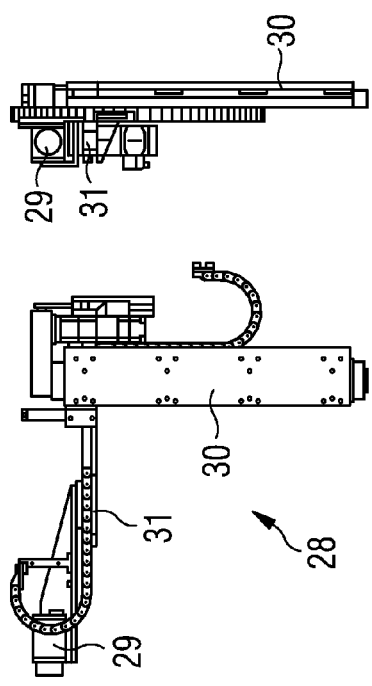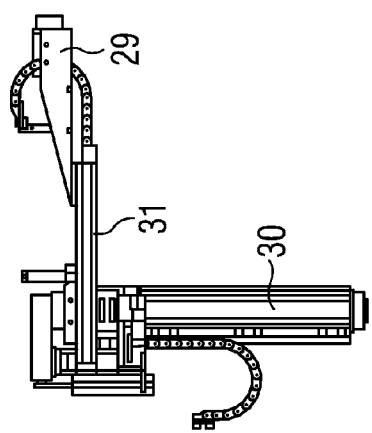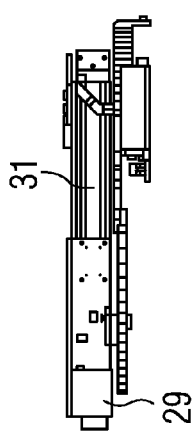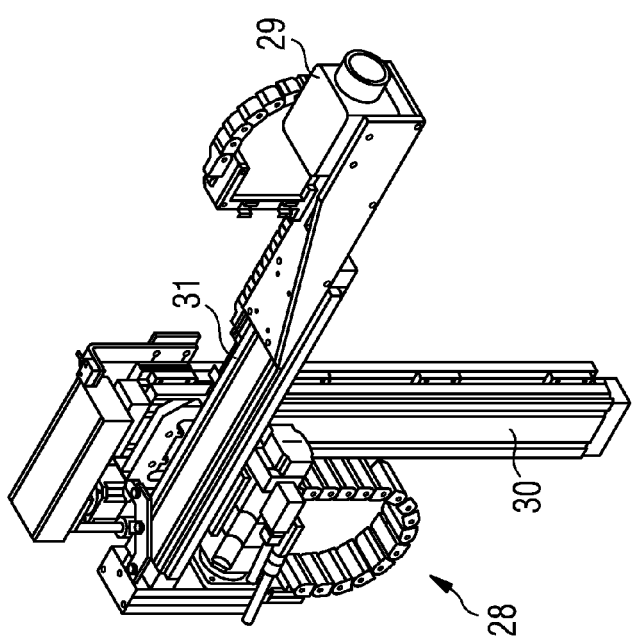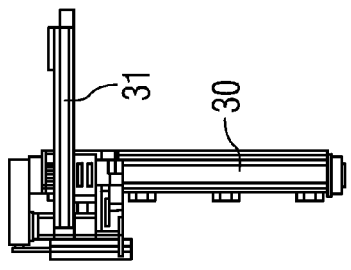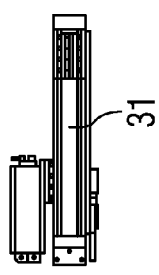

TESTING SYSTEM FOR EXAMINING TURBINE BLADES

CROSS REFERENCE TO RELATED APPLICATIONS

This application is the US National Stage of International Application No. PCT/EP2010/069947, filed Dec. 16, 2012 and claims the benefit thereof. The International application claims the benefits of German application No. 10 2010 018 013.0 DE filed Apr. 23, 2010. All of the applications are incorporated by reference herein in their entirety.

FIELD OF INVENTION

The invention relates generally to a testing system for examining turbine blades and particularly to a testing system for examining the coating and open cooling-air holes of turbine blades, for instance of gas turbine blades.

BACKGROUND OF INVENTION

The examination of the coating and of open cooling-air holes on turbine blades is realized by means of an infrared camera. This involves excitation by means of hot air and flash lamps and recording of the resultant heat flux by an infrared camera. In order to examine suitable regions and/or image portions, the component, such as for example a turbine blade, and the camera must be correspondingly positioned.

A known testing system is described on the basis of FIGS. 1 and 2. In the case of the known testing system, the infrared camera is positioned by means of an industrial robot. The turbine blade is fixed on a rotary table. The rotary table usually has two receptacles for turbine blades, which are arranged such that one receptacle is located in an enclosure of the robot for testing while the other receptacle is externally accessible for the loading or removal of the turbine blade.

The tester's working place, located outside the enclosure, is shielded from flash and flow noises. In a testing procedure, firstly the type of test, the testing position and the focus of the infrared camera are established. Then, the parameters are transferred into a system database. The robot travels over a testing path, in order in this way to position the infrared camera.

WO 98/05949 A1 discloses a testing system for testing gas turbine blades for delamination, with a rotating device for the blade and a three-axis positioning device for an IR camera. To check the internal structure, hot air may be introduced into the blade.

EP 1 739 409 A1 discloses a testing system for determining the location and the angular position of holes in a turbine blade, with a fixed-in-place receptacle for the blade, a positioning device for an IR camera and a radiant heater for heating the turbine blade.

US 2008/237466 A1 discloses a testing system for determining the gas flow through holes in a turbine blade, with a fixed-in-place receptacle for the turbine blade and an IR camera arranged on a robot arm. Warm air is passed through the receptacle and through the turbine blade.

WO 03/038403 A2 discloses an inspection system for a turbine blade, with a fixed-in-place receptacle for holding and introducing air or gas into the turbine blade. A number of mirrors are arranged around the receptacle, in order to make more than one side or edge of the turbine blade accessible to an IR camera.

U.S. Pat. No. 5,111,046 A discloses a device for the inspection of channels of a turbine blade, with a fixed-in-place receptacle for holding and introducing air or gas into the turbine blade and an IR camera for recording heating-up and cooling-down processes.

SUMMARY OF INVENTION

It is the object of the invention to simplify the testing of turbine blades.

This object is achieved by the features of the independent claim(s). Advantageous developments of the invention are defined in the dependent claims.

The invention is directed to a testing system for examining the coating and open cooling-air holes of turbine blades, in particular of gas turbine blades, having a rotating-pivoting device for positioning the turbine blade, a rotatable air duct, arranged on the rotating-pivoting device, for introducing into the turbine blade air at a temperature higher or lower in comparison with the turbine blade and a positioning device for an infrared camera with two degrees of freedom. The contactless and nondestructive testing of the turbine blade is significantly simplified by the invention. As a departure from the previous procedure, in which the IR camera was moved around the turbine blade by an industrial robot, the component is now rotated and pivoted, while the camera is moved by a positioning device, such as for example a motorized ZX stage. A rotatable air duct allows the feeding of air at a higher or lower temperature in comparison with the turbine blade or a gas at a higher or lower temperature in comparison with the turbine blade (20) into the turbine blade even during rotation of the component. Overall, it does not matter whether the air or gas is heated or cooled, but only that there is a temperature difference between the air or gas on the one hand and the turbine blade on the other hand that is great enough to allow it to be detected by the IR camera. Thus, for example, the turbine blade could also be heated or cooled with respect to the air or the gas that is used. Typically, however, heated and cooled air or heated and cooled gas is used, the heated air (or the heated gas) and the cooled air (or the cooled gas) being fed to the turbine blade alternately, in order to counteract excessive heating up or excessive cooling down of the turbine blade during the testing.

This device is less costly than a solution with an industrial robot; the cost saving may be around € 500000 per testing system. Moreover, a significantly smaller testing installation, which is to a certain extent mobile, is possible. Since the camera is only positioned, that is to say neither rotated nor tilted, the alignment of the camera always remains constant. The constant horizontal position is extremely important for a liquid-cooled IR camera, since a positional change leads to deterioration of the image quality, caused by heat flux and Stirling cooler effects.

The rotating-pivoting device may have a base plate with a turntable that is rotatable about an axis of rotation. This is a solution which can be integrated well, is space-saving and is well suited for receiving a turbine blade.

The base plate may be pivotable about a pivot axis, which is perpendicular to the axis of rotation. The pivot axis represents a second degree of freedom, so that the component can be positioned for a full examination.

The rotating-pivoting device may be arrestable, steplessly or by steps, in the rotating and/or pivoting direction. This makes it possible for the position of the turbine blade to be fixed, for example in predetermined testing positions. A motor-driven rotating-pivoting device is also possible. It is then possible to dispense with the arresting.

The rotating-pivoting device may have a blade clamping device, for instance a pneumatic blade clamping device, for fixing the turbine blade. The rotating-pivoting device can consequently be used for fixing and positioning the turbine blade. The fixing can securely hold the turbine blade on the rotating-pivoting device even during pivoting and/or rotating movements.

The air duct may have a high-temperature-resistant rotary connector. This makes it possible for the blade, including the hot air or gas supply, to rotate.

The rotary connector may be arranged in the region of the axis of rotation. Thus, for example, a hollow axis of rotation may serve as a feed for the heating air. This reduces the structural complexity.

The positioning device for the IR camera may have a horizontal degree of freedom and a vertical degree of freedom. This simplified camera positioning is a low-cost solution, since only two degrees of freedom are used, for example realized by a ZX stage. With the horizontal and vertical degrees of freedom, the camera can be positioned sufficiently to test all the regions of the turbine blade.

The testing system may have an infrared camera arranged on the positioning device. The camera may already be a component part of the testing system or it may be retrofitted.

The testing system may have a basic frame with a testing booth, in which the rotating-pivoting device and the positioning device are arranged. The basic frame may carry the rotating-pivoting device, the rotatable air duct and the positioning device for the infrared camera. This makes it possible for the testing system to have a stable base and allows the testing system to be easily moved.

The testing booth may be closable. Thus, the surroundings and the operating personnel can be protected from noise and other distractions. The testing booth may be closed in an airtight or almost airtight manner, in order to prevent or reduce an escape of the air or a gas at the higher or lower temperature in comparison with the turbine blade that is used for the testing.

The testing system may have an air extraction device, in order for the air or gas that is fed in to be extracted again and possibly recirculated. Thus, a small negative pressure may be produced in the testing booth, preventing the air or the gas from escaping from the testing booth. In addition or alternatively, the testing system may also comprise an air conditioning device for the testing booth, whereby the temperature inside the testing booth can be set and kept largely constant during the testing procedure.

The testing system may have an information and/or operator control unit arranged outside the testing booth. Thus, the testing can be monitored and/or controlled even when the testing booth is closed.

The testing system may have at least one flash lamp for flash-thermographic measurements. Extended measurements are thereby possible.

The testing system may have an ultrasonic device for ultrasonic excitation of the turbine blade. Extended measurements are thereby possible.

BRIEF DESCRIPTION OF THE DRAWINGS

The invention is described in more detail below on the basis of the drawings, in which:

FIGS. 3-7 show various views of a basic frame with a testing booth of the testing system according to the invention;
FIG. 8 shows a perspective representation of the basic frame according to the invention;
FIGS. 9-14 show various views of a rotating-pivoting device according to the invention;
FIGS. 17-20 show various views of a turntable with an air duct according to the invention;
FIGS. 21-27 show various views of a positioning device with an infrared camera according to the invention.

DETAILED DESCRIPTION OF INVENTION

Figure 1:
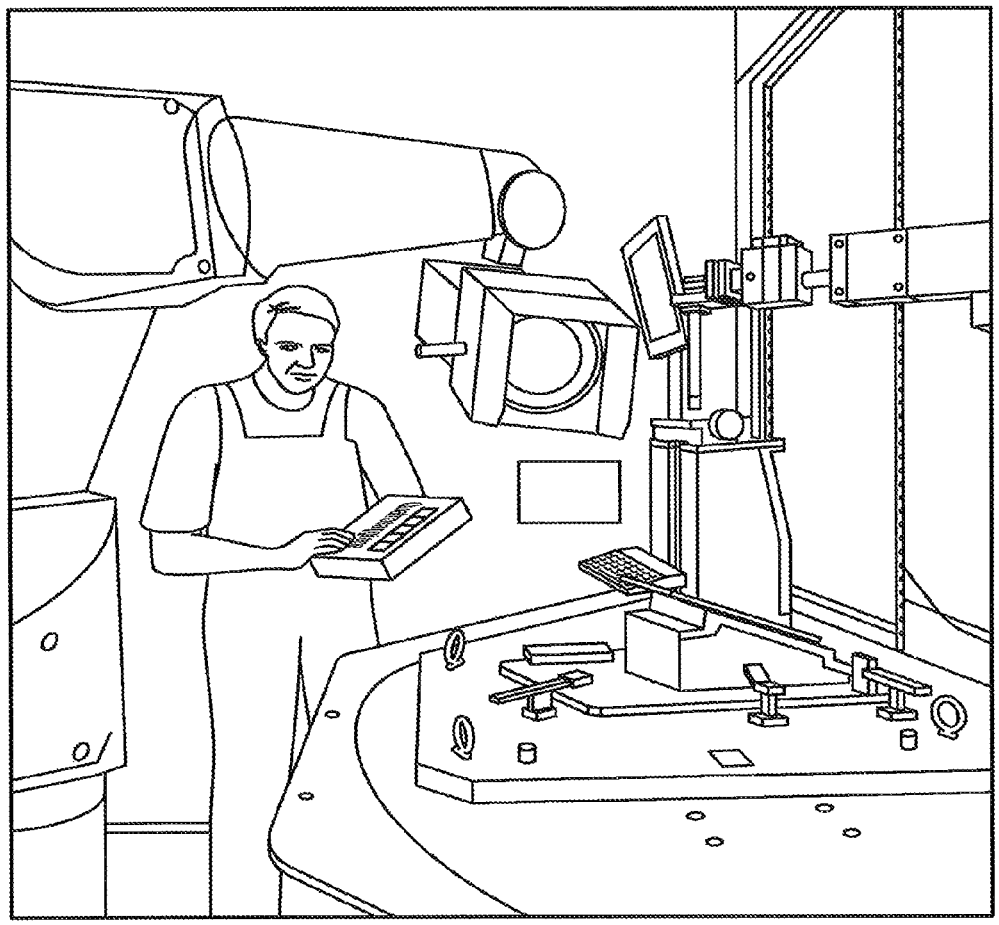
FIG. 1 shows a known testing system for a turbine blade.
Figure 2:
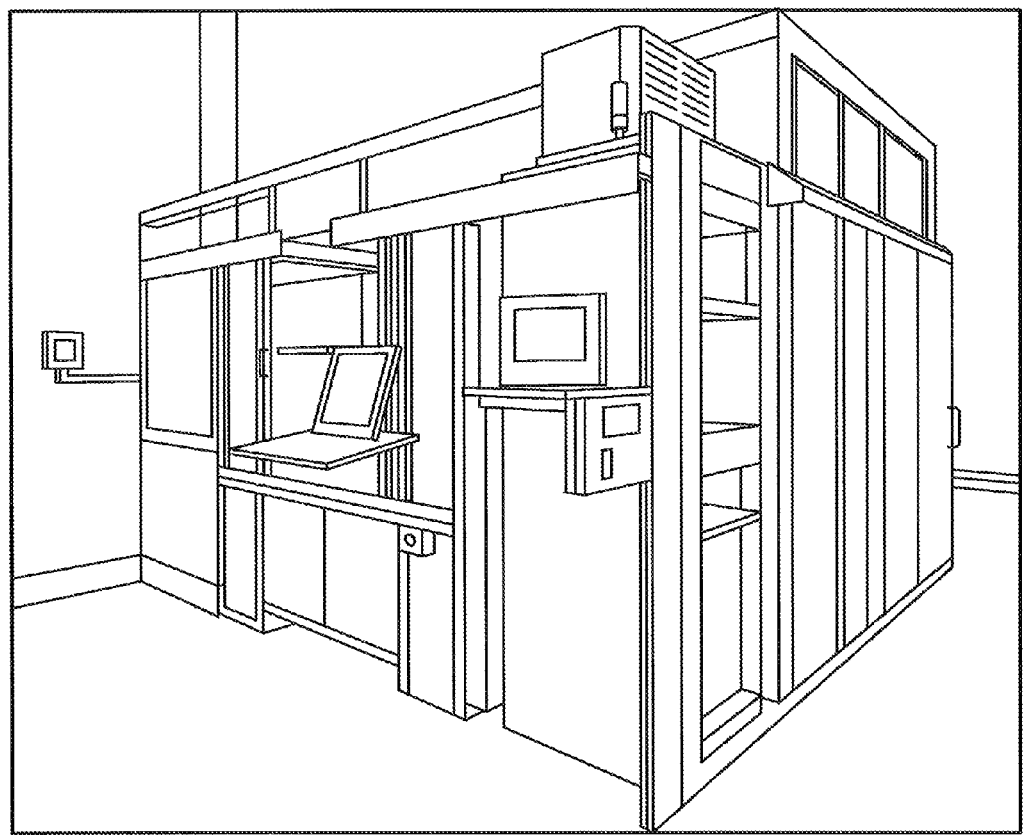
FIG. 2 shows a further representation of the known testing system for a turbine blade.

The drawings merely serve for explaining the invention and do not restrict it. The drawings and individual parts are not necessarily to scale. The same reference numerals designate the same or similar parts.

FIGS. 3 to 7 show a testing system 1 for examining turbine blades or similar blades in various views.

FIGS. 3 to 5 show various side views, FIG. 6 a plan view and FIG. 7 a perspective view. In the testing system 1, the coating and open cooling-air holes of the turbine blade are investigated.

The testing system 1 is based on a basic frame 2, which consists for example of aluminum sections, it being possible for the open surfaces that are produced between the individual sections to remain open or to be covered with a panel 3.

The testing system 1 may stand on feet, as represented, so that a forklift truck or elevating-platform truck can lift up the testing system 1 and relocate it. Alternatively, the testing system 1 may stand on rollers or wheels, which are preferably arrestable.

Arranged on the basic frame 2 is a testing booth 4, which can be closed with two doors 5. The testing booth 4 may be of an airtight or almost airtight form, in order to avoid an escape of air or gas. The testing booth 4 is covered all around with panels 3, which may be sealed with respect to the aluminum sections. On the upper side of the testing booth there may also be a closable loading opening, which makes it possible for heavy parts that are to be tested to be introduced with the aid of a crane.

Arranged on the upper side of the testing system 1 is an information unit 6. The information unit 6 may for example consist of three lights with the colors green, yellow or orange and red. These three lights indicate the status of the testing system 1 as follows. Green indicates trouble-free operation, yellow or orange indicates a fault or warning and red indicates a malfunction.

Furthermore, the testing system 1 is equipped with an operator control unit 7. The operator control unit 7 may comprise a computer, such as for example a laptop or the monitor and keyboard of a permanently installed computer that is especially set up for the testing system and is connected to a controlling and/or monitoring system of the testing system 1. For the sake of simplicity, all that is shown of the operator control unit 7 is the mounting for the computer. The mounting for the operator control unit 7 is arranged in the region of the doors 5, in order to make it possible for the testing system 1 to be easily operated. The mounting can be adjusted in several or all degrees of freedom, in order in this way to allow it to be adapted to the operating personnel.

FIG. 8 shows a further example of the testing system 1 in a perspective representation. In a way similar to the testing system 1 from FIGS. 3 to 7, the testing system represented in FIG. 8 comprises a basic frame 2, which is now completely covered with panels 3 on the wall surfaces. The upper part, the top of the testing booth 4 as it were, is formed as a closable loading opening. In a front region of the testing system 1, the testing booth 4 is closed with closable doors 5.

The information unit and the operator control unit are not present in this testing system 1. The testing system 1 can be operated and monitored for example means of a stored-program controller (SPC) or some other network.

Arranged in the testing booth 4 is the actual testing arrangement for the turbine blade. The individual component parts of the testing arrangement are described in conjunction with the following figures.

In FIGS. 9 to 14, a rotating-pivoting device 8 of the testing system 1 is represented in detail in various views. Of these, FIGS. 9 to 11 show various side views, FIG. 12 a plan view and FIGS. 13 and 14 various perspective views.

The rotating-pivoting device 8 comprises a base plate 9, which in a starting position or basic position is horizontally aligned. The base plate 9, and consequently the rotating-pivoting device 8 as a whole, is fastened on the basic frame 2 by fastening elements 10. The fastening may be performed with a screw connection, a clamping connection or a similarly suitable fastening.

Arranged between the fastening element 10 and the base plate 9 is a pivoting device 11. By means of the pivoting device 11, the base plate 9 can be pivoted about a pivot axis 12. The pivot axis 12 runs substantially horizontally. The pivoting movement of the base plate 9 is performed by a motor 13. Fitted on the motor 13 is a gear wheel, which engages in an arcuate toothed rack 14. The toothed rack 14 has for example the form of a segment of a circle, having for example an angular region of about 90°. The toothed rack 14 is connected to the pivot axis 12 by way of a linkage or some other suitable mechanism, so that, when the motor 13 is actuated, the movement of the toothed rack 14 is transformed into a pivoting movement of the base plate 9.

The positioning of the base plate 9 along the path of the pivoting movement may be arrestable, for example by the holding force of the motor 13 or by other means, such as for example engaging pins.

Arranged on the base plate 9 is a turntable 15, which can rotate about an axis of rotation 16. The axis of rotation 16 runs at right angles to the pivot axis 12, therefore is in this case oriented perpendicularly. The turntable 15 has on its outer circumferential surface, or at least on part of the circumferential surface, the contour of a gear wheel, in which a gear wheel fitted on a motor 17 engages. When the motor 17 is actuated, the turntable 15 is rotated correspondingly.

A clamping device 18 for fixing the turbine blade is provided on the turntable 15. The clamping device 18 comprises a perpendicularly running rod of a stand, fastened on which is a height-adjustable and rotatable clamping grip.

Also arranged on the turntable 15 is a receptacle 19 for the turbine blade. The receptacle 19 may for example comprise a recess, an elevation, a compressible material or a combination thereof.

Figure 15:
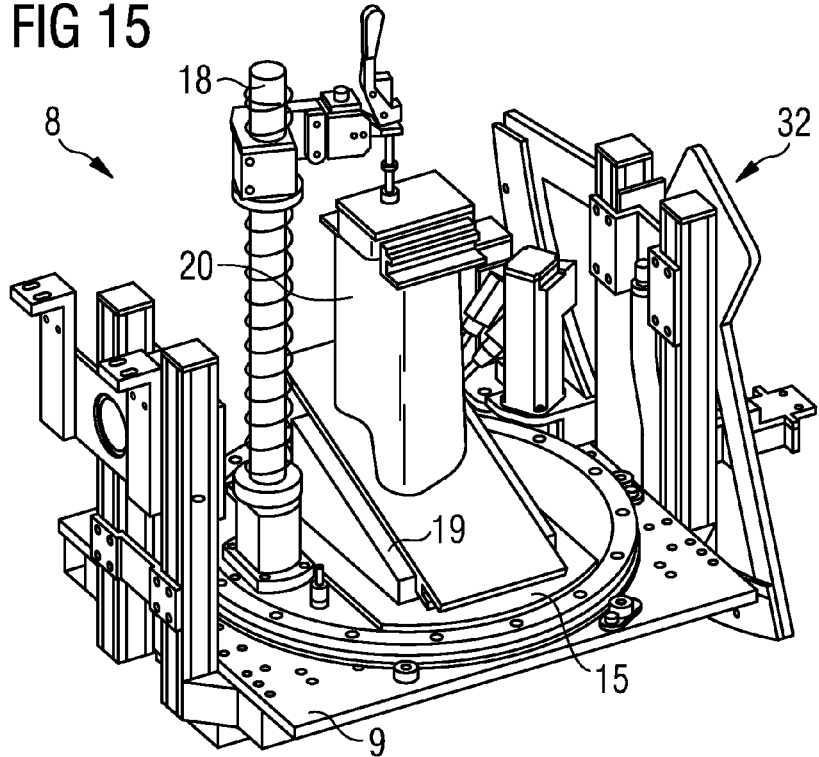
FIGS. 15, 16 show perspective representations of the rotating-pivoting device according to the invention.
Figure 16:
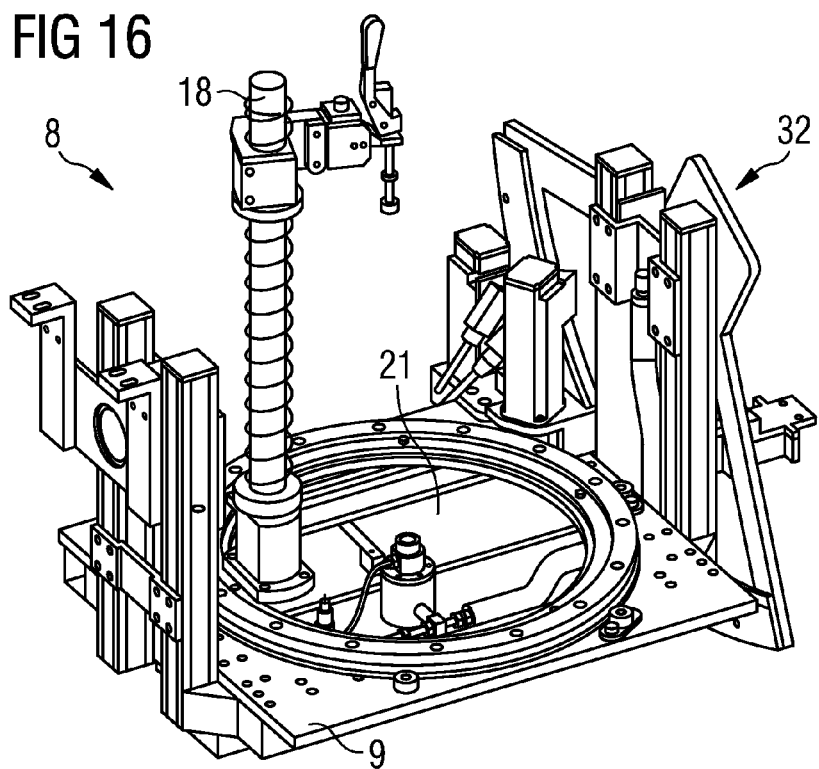

FIGS. 15 and 16 show two perspective representations of the rotating-pivoting device 8. In FIG. 15, a turbine blade 20 is fastened in the rotating-pivoting device 8. The turbine blade 20 is arranged on the turntable 15 by means of the receptacle 19. The clamping device 18 engages in an upper region of the turbine blade 20, in order to fix it on the turntable 15 by bracing. Any adapters or intermediate pieces that are required, both between the clamping device 18 and the turbine blade 20 and between the receptacle 19 and the turbine blade 20, may either be assigned to the clamping device 18 or the receptacle 19 or be assigned to the turbine blade 20.

FIG. 16 shows the rotating-pivoting device 8 without the turbine blade 20. The turntable 15 is also represented as broken through, in order to allow a view of the air duct 21 lying thereunder. The air duct 21 serves the purpose of conducting warm or hot air or a gas into the interior of the turbine blade 20 during the testing. The air duct 21 is designed in such a way that the feeding in of the air or gas is ensured even when the turntable 15 is rotating about the axis of rotation 16. An air duct is similarly present in the region of the pivot axis 32.

In FIGS. 17 to 20, the air duct 21 is represented in detail. Of these, FIG. 17 shows a side view and FIG. 18 a plan view of the turntable 15; FIGS. 19 and 20 respectively show perspective views of the upper side and the underside of the turntable 15.

The air duct 21 comprises a central high-temperature-resistant rotary connector 22, which is arranged along the axis of rotation 16. The rotary connector 22 comprises a hollow spindle communicating with openings in the receptacle 19. The turntable 15 rotates about this hollow spindle, so that, even when the turntable 15 is rotating, air or gas flows into the receptacle and then into the turbine blade 20 arranged therein or thereupon.

Two different gases or gases of the same type (for example air) set to different temperatures may be fed in via a first feed line 23 and a second feed line 24. Thus, for example, the first feed line 23 may be used for feeding in cooled air and the second feed line 24 for feeding in heated air. By alternately feeding in cooled and heated air, excessive heating or excessive cooling of the turbine blade during testing can be avoided. In addition or alternatively, there is also the possibility of cooling the turbine blade before feeding in the heated air by feeding in cooled air, in order to increase the contrast when testing by means of heated air. Testing by means of cooled air and increasing the contrast by preheating the turbine blade by means of heated air is likewise possible. The feeding in of the air may in this case be controlled by means of valves, such as valve 25 represented in FIGS. 17-18.

A further feed line, which is formed as a compressed-air feed line 26, leads to the rotary connector 22 and is led through the rotary connector 22, in order to arrive at a valve 27 arranged on the turntable 15. This valve 27 turns with the turntable 15, as does part of the feed line 26. The compressed-air feed line 26 may be used for providing compressed air for a pneumatic blade clamping device. As already mentioned, the two feed lines 23 and 24 may be used for feeding in different gases or gases set to different temperatures. Different types of gases may then be used either individually or in a mixed state. It is similarly possible that one of the feed lines 23 or 24 is used for extracting air or gas from the testing booth 4.

The rotary connector 22 is formed as a two-channel rotary connector and is designed in such a way that the lines located in a lower part of the rotary connector 22 are fixed in place, while the hollow spindle and the line of the upper part of the rotary connector 22 turn with the turntable 15. Fixed in place means here with respect to the turntable 15, but allows a pivoting movement with the pivoting device 11.

FIGS. 21 to 25 show the positioning device 28 of the testing system 1 in various views. Of these, FIGS. 21 to 23 show the positioning device 28 in various side views, FIG. 24 in a plan view and FIG. 25 in a perspective representation. The positioning device 28 carries an infrared camera 29, which can be positioned in two degrees of freedom by means of the positioning device 28.

The positioning device 28 comprises a first, perpendicularly arranged linear unit 30, which may be fastened on an aluminum section of the basic frame 2. A second, horizontally arranged linear unit 31 can be moved along the first linear unit by means of a motor. As a result, the first degree of freedom of the positioning device 28 is realized in the Z direction. The linear units are represented in FIGS. 26 and 27 without a camera, FIG. 26 showing a side view and FIG. 27 a plan view.

A carriage or a fastening unit for the infrared camera 29 can be moved along the second linear unit 31 by means of a further motor. As a result, the second degree of freedom of the positioning device 28 is realized in the X direction.

The infrared camera 29 is moved in two degrees of freedom by means of the positioning device 28, the position or alignment of the camera 29 remaining unchanged. Consequently, the infrared camera maintains a constant horizontal position, which leads to an increase in the image quality.

The component parts of the testing system 1 described in conjunction with FIGS. 9 to 27, to be specific the rotating-pivoting device 8, the turntable 15, the air duct 21 and the positioning device 28, are arranged on the basic frame 2 or in the testing booth 4. To be more precise, the rotating-pivoting device 8 is fastened on sections or panels of the basic frame 2, whereby the turntable 15 and the air duct 21 are likewise fastened. The positioning device 28 is likewise fastened on sections or panels of the basic frame 2, to be precise in such a way that the infrared camera 29 can be positioned in relation to the turntable 15, in order to be able to record all the regions of the turbine blade 20 that are to be tested. Recordings of the turbine blade 20 are possible both in the basic position and in any combinations of the pivoting movement and the rotating movement.

When a testing booth 4 is used, it is possible that the complete rotating-pivoting device 8, the turntable 15, the air duct 21 and the positioning device 28 with the infrared camera 29 are arranged within the testing booth 4. In order for example to reduce the enclosed volume of the testing booth 4, the component parts of the testing system 1 may be arranged within the basic frame 2 in such a way that merely the upper side of the base plate 9 and part of the positioning device 28 with the infrared camera 29 are arranged within the testing booth 4. Component parts of the testing booth 4, such as for example bottom or side regions, may be of a flexible configuration, in order to facilitate pivoting movements of the rotating-pivoting device 8.

Furthermore, the testing system 1 may comprise a flash lamp (not represented) for flash-thermographic measurements. The testing system 1 may also have an ultrasonic device for ultrasonic excitation. With these additional devices, the scope of the testing can be increased.

A procedure for testing a turbine blade 20 in the testing system 1 is described below. After opening the doors 5 of the testing booth 4, the turbine blade 20 is inserted into the receptacle 19 of the turntable 15 and fixed there with the clamping device 18. In order to facilitate the insertion, the rotating-pivoting device 8 may be moved into an inserting position. The testing which then follows may be carried out with the doors 5 open or closed. Moreover, loading by means of a crane through the open loading opening is possible.

For the testing, the operator of the testing system 1 selects a testing program, which may take place for example by means of the operator control unit 7. The movements of the rotating-pivoting device 8, the turntable 15 and the positioning device 28 are predetermined by the testing program or the input of individual parameters. Also predetermined are the feeding in of air, warm air or gas through the air duct 21 and the control of the infrared camera 29, such as for example the triggering times and parameters. Flashlight and ultrasound are likewise controlled by the testing program.

During the testing of the turbine blade 20, the status of the testing system 1 is indicated by means of the information unit 6. The status and further details of the testing system 1 may be indicated on the operator control unit 7. A log and/or data of the testing may likewise be made available on the operator control unit 7 and/or made available via a network or a data carrier of further computers.

For carrying out the testing program, the testing system 1 may have a dedicated control computer, which controls and monitors the testing procedure and/or controls the communication. It is similarly possible that the testing system 1 is controlled by an external computer, such as a management or control unit of the factory or a computer of the operator control unit 7.

The invention claimed is:

1. A testing system for examining the coating and open cooling-air holes of turbine blades, comprising:
   a positioning device for an infrared camera with solely a horizontal degree of freedom and a vertical degree of freedom such that the infrared camera is not rotatable or tiltable,
   a rotating-pivoting device for positioning the turbine blade about an axis of rotation and about a pivot axis that is perpendicular to the axis of rotation,
   a rotatable air duct arranged on the rotating-pivoting device for introducing into the turbine blade air at a temperature higher or lower in comparison with the turbine blade, and
   an infrared camera arranged on the positioning device;
   wherein the rotatable air duct comprises a rotary connector including a hollow spindle, wherein the hollow spindle is in flow communication with multiple openings located adjacent one another side by side in the receptacle such that air flows into the receptacle and into a blade disposed in the receptacle during operation of the testing system.

2. The testing system as claimed in claim 1, wherein the rotating-pivoting device comprises a base plate with a turntable that is rotatable about the axis of rotation.

3. The testing system as claimed in claim 2, wherein the base plate is pivotable about the pivot axis, which is perpendicular to the axis of rotation.

4. The testing system as claimed in claim 1, wherein the rotating-pivoting device is arrestable or motor-driven in the rotating and/or pivoting direction.

5. The testing system as claimed in claim 1, wherein the rotating-pivoting device comprises a blade clamping device for fixing the turbine blade.

6. The testing system as claimed in claim 1, wherein the air duct has a high-temperature-resistant rotary connector.

7. The testing system as claimed in claim 6, wherein the rotary connector is arranged in the region of the axis of rotation.

8. The testing system as claimed in claim 1, further comprising a basic frame with a testing booth, in which the rotating-pivoting device and the positioning device are arranged.

9. The testing system as claimed in claim 8, wherein the testing booth is closable.

10. The testing system as claimed in claim 8, further comprising an air extraction device and/or an air conditioning device for the testing booth.

11. The testing system as claimed in claim 8, further comprising an information and/or operator control unit arranged outside the testing booth.

12. The testing system as claimed in claim 1, further comprising at least one flash lamp for flash-thermographic measurements.

13. The testing system as claimed in claim 1, further comprising an ultrasonic device for ultrasonic excitation of the turbine blade.

14. The testing system as claimed in claim 2, further comprising a receptacle on the turntable for receiving a turbine blade.

\* \* \* \* \*